(12) United States Patent
Müller et al.

(10) Patent No.: US 9,180,103 B2
(45) Date of Patent: Nov. 10, 2015

(54) PLASTER HAVING ADJUSTABLE OCCLUSION

(71) Applicant: LTS LOHMANN THERAPIE-SYSTEME AG, Andernach (DE)

(72) Inventors: Walter Müller, Andernach (DE); Patrick Mohr, Bad Breisig (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 0 days.

(21) Appl. No.: 14/346,527

(22) PCT Filed: Sep. 25, 2012

(86) PCT No.: PCT/EP2012/068828
§ 371 (c)(1),
(2) Date: Mar. 21, 2014

(87) PCT Pub. No.: WO2013/045420
PCT Pub. Date: Apr. 4, 2013

(65) Prior Publication Data
US 2014/0234395 A1    Aug. 21, 2014

(30) Foreign Application Priority Data
Sep. 26, 2011    (DE) .......................... 10 2011 114 411

(51) Int. Cl.
| | | |
|---|---|---|
| *A61F 13/02* | (2006.01) |
| *A61K 9/70* | (2006.01) |
| *A61K 9/00* | (2006.01) |
| *A61L 15/22* | (2006.01) |
| *A61L 15/44* | (2006.01) |
| *A61L 15/58* | (2006.01) |
| *A61L 15/42* | (2006.01) |
| *A61L 15/48* | (2006.01) |
| *A61K 31/167* | (2006.01) |
| *A61K 31/196* | (2006.01) |
| *A61K 31/245* | (2006.01) |

(52) U.S. Cl.
CPC ............ *A61K 9/7053* (2013.01); *A61K 9/0014* (2013.01); *A61K 9/7023* (2013.01); *A61K 9/7061* (2013.01); *A61K 9/7084* (2013.01); *A61K 31/167* (2013.01); *A61K 31/196* (2013.01); *A61K 31/245* (2013.01); *A61L 15/225* (2013.01); *A61L 15/42* (2013.01); *A61L 15/44* (2013.01); *A61L 15/48* (2013.01); *A61L 15/58* (2013.01); *A61L 2300/402* (2013.01); *A61L 2300/41* (2013.01)

(58) Field of Classification Search
CPC .. A61K 9/7023; A61K 9/7084; A61K 9/0014
See application file for complete search history.

(56) References Cited

U.S. PATENT DOCUMENTS 6,235,306 B1    5/2001    Miranda et al.

FOREIGN PATENT DOCUMENTS

| EP | 0379045 A1 | 7/1990 |
| WO | WO 93/00058 A1 | 1/1993 |
| WO | WO 01/91718 A2 | 12/2001 |

*Primary Examiner* — Carlos Azpuru
(74) *Attorney, Agent, or Firm* — ProPat, L.L.C.

(57) ABSTRACT

Transdermal or topical plasters containing active ingredient are provided that include a non-occlusive back layer, a matrix formed from of one or more polymer layers having at least one pharmaceutical active ingredient in one or more of the layers, in which the structure-forming base polymers of the layer(s) are non-occlusive or only slightly occlusive and a second polymer that has a low water-vapor permeability and that is immiscible or only very slightly miscible with the base polymer is dispersed in at least one of the polymer layers.

24 Claims, 4 Drawing Sheets

PLASTER HAVING ADJUSTABLE OCCLUSION

CROSS-REFERENCE TO RELATED APPLICATIONS

This application is being filed under 35 U.S.C. §371 as a National Stage Application of pending International Application No. PCT/EP2012/068828 filed Sep. 25, 2012, which claims priority to parent German Patent Application No. 10 2011 114 411.4, filed Sep. 26, 2011. Both International Application No. PCT/EP2012/068828 and German Patent Application No. 10 2011 114 411.4 are hereby incorporated by reference herein in their entirety.

FIELD OF THE INVENTION

The present invention relates to transdermal or topical plasters, particularly transdermal or topical plasters exhibiting adjustable occlusion.

BACKGROUND OF THE INVENTION

For the transdermal or topical administration of active ingredients, the stratum corneum is a lipophilic barrier which limits the uptake of active ingredient. One of the most effective, and a physical method employed virtually for every systemically acting transdermal system, for lowering the barrier function of the stratum corneum is occlusion. The occlusion is achieved through the use of virtually water vapor-impermeable materials for the backing layers of transdermal systems, and/or through the use of water vapor-impermeable formulations of adjacent layers and/or the active ingredient layer or layers. A schematic representation of a patch of this kind is shown by FIG. 1. For the backing layers, polyester films are used in the great majority of cases. In principle, however, there is nothing against other films of low water vapor permeability, such as films of polyethylene or polypropylene, for example. As polymers or pressure-sensitive adhesives with low water vapor permeability, for example, polyisobutylene or block polymers of styrene and butadiene or of styrene and isoprene are used.

Topical systems with, for example, nonsteroidal anti-inflammatory drugs, especially, have a size which corresponds to the area of the treatment zone, and hence a size which necessitates a certain stretchability on the part of the patch system in order to increase wear comfort. Since, in the thickness appropriate for this purpose, the aforementioned occlusive materials for the backing layer do not possess sufficient stretchability or elasticity, textile materials are often employed for such patches. A disadvantage of these textile backing layers, however, is that their open porosity gives them very high water vapor permeability, meaning that they do not create occlusive conditions. As a consequence of this, occlusion in the case of patches with textile backing layers must be achieved through other water vapor-impermeable layers, or at least other layers which are less permeable to water vapor. For this purpose, of course, it is not possible to use nonstretchable and inelastic materials. The simplest way of achieving occlusion is through the use of pressure-sensitive adhesives of low water vapor permeability, such as pressure-sensitive adhesives based on polyisobutylene or on block polymers of styrene and butadiene or isoprene. A disadvantage in that case, however, is that these pressure-sensitive adhesives attach only very poorly to the skin, which becomes moist under occlusion, and are easily wholly or partly detached, especially in the joint region.

WO 01/91718 A2 describes a two-phase matrix, where a polyacrylate phase containing active ingredient is dispersed in an outer, self-adhesive formulation based on polyisobutylene or styrene-butadiene-styrene block polymers. A disadvantage here is that the occlusion effect is always at its maximum at practical layer thicknesses, and the outer phase, as already stated above, adheres very poorly to moist skin. The only advantage of such a matrix is that the active ingredient is located in a polymer with a relatively high saturation solubility.

Polyacrylate adhesives or silicone adhesives perform substantially better under such conditions, but their high water vapor permeability means that they are unable themselves to create occlusive conditions. In accordance with the prior art, therefore, the use of polyacrylate or silicone adhesives has been considered to necessitate multilayer matrices with layers differing in their composition, thereby complicating the production process and pushing up the production cost, which is an important factor for this product group.

SUMMARY OF ADVANTAGEOUS EMBODIMENTS OF THE INVENTION

There exists, consequently, the need for occlusive patches having a textile, stretchable backing layer and having pressure-sensitive adhesives that attach well to moist skin and are based on polyacrylates or silicone adhesives, these patches possessing an extremely simple construction and being easy to produce.

DETAILED DESCRIPTION OF ADVANTAGEOUS EMBODIMENTS OF THE INVENTION

Figure 2:
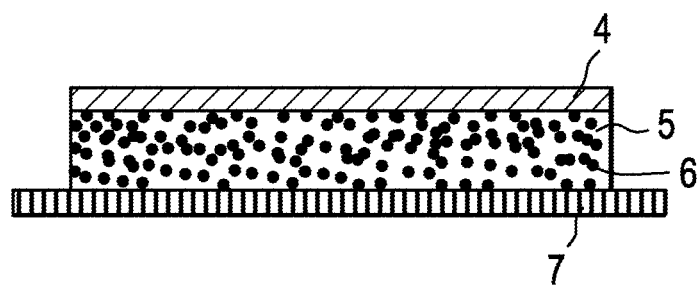
FIG. 2 is a schematic illustration of an exemplary inventive patch with adjustable occlusion.

Surprisingly, the solution to the problem has been found, in accordance with the invention, to lie in dispersing a polymer of low water vapor permeability, such as polyisobutylene or a block polymer of styrene and butadiene or isoprene, for example, in the matrix layer or layers constructed from water vapor-permeable pressure-sensitive adhesives. By virtue of their physicochemical properties, the active ingredients are very largely present in the polyacrylate phase of such a matrix. Through the amount of water vapor-impermeable polymer and through the thickness of the matrix it is possible to vary the occlusion effect within wide limits. At its most simple, therefore, a patch of the invention consists of a textile backing layer, an active ingredient matrix layer based on polyacrylate or silicone adhesives with water vapor-impermeable polymer dispersed therein, and a protective layer to be removed prior to use. The construction of a patch of this kind is depicted in FIG. 2.

The invention accordingly provides a transdermal or topical, active ingredient patch having a nonocclusive backing layer, a matrix, formed from one or more polymer layers, with at least one active pharmaceutical in in one or more of the layers, which is characterized in that the structure-forming base polymers of the layer or layers are nonocclusive or minimally occlusive and in at least one of the polymer layers there is a second polymer dispersed, which is immiscible or very minimally miscible with the base polymer and has a low water vapor permeability.

The backing layer consists preferably of a textile material, more particularly of a woven fabric or nonwoven web material, or of a composite of such materials. Examples of materials contemplated here include cotton, viscose, polyesters, polyamides, polyurethane, or polypropylene. Polyurethane is also suitable as a water vapor-permeable film material.

The structure-forming base polymer of the matrix layer, which comes into contact with the skin on application, is preferably a pressure-sensitive adhesive (PSA). Suitable PSAs are, for example, polyacrylate adhesives or silicone adhesives. The matrix is preferably of single-layer construction.

The polymer with low water vapor permeability may be, for example, polyisobutylene, a styrene-isoprene-styrene block polymer, or a styrene-butadiene-styrene block polymer. The dispersed phase of this polymer preferably has an average particle size of 5 to 50 µm, more particularly 7 to 40 µm, very preferably 10 to 30 µm. The fraction of the dispersed particles in the matrix is generally between 5 and 50 wt %, preferably 7 and 40 wt %, more particularly 10 and 30 wt %.

The basis weight of the matrix is generally between 50 and 400 g/m$^2$, preferably between 60 and 300 g/m$^2$, more particularly between 70 and 200 g/m$^2$.

The active pharmaceutical ingredient may be a nonsteroidal anti-inflammatory drug (NSAID, for non-steroidal anti-inflammatory drug). These agents are often used locally externally in the region of joints, particularly the extremities. It is exactly at these sites of application, subject to severe mechanical stress, that the TTS of the invention prove particularly advantageous. Without any claim to completeness, the active ingredients involved are those from the group of diclofenac or a pharmaceutically acceptable salt thereof, ketoprofen, ibuprofen, flurbiprofen, naproxen, tiaprofenic acid, indomethacin, piroxicam, tenoxicam, meloxicam, flufenaminic acid, or mefenaminic acid. Preferred diclofenac salts are, for example, diclofenac sodium salt, diclofenac potassium salt, diclofenac diethylammonium salt, or the dihydroxyethylpyrrolidine salt of diclofenac.

Further suitable active ingredients are topically active analgesics, e.g., lidocaine or tetracaine.

Besides the polymers and active ingredients already mentioned, there are also numerous other excipients that can be employed, of the kind known in the art for use in TTS.

Thus, for example, permeation enhancers may be used, preferably in the internal phase of the matrix. Suitable permeation enhancers are compounds from the group of low molecular mass, monohydric or polyhydric alcohols, fatty acids (preferably oleic acid), fatty alcohols, fatty alcohol ethers, polyoxyethylated fatty alcohols, fatty acid esters (especially monoglycerides and monoesters of propylene glycol), sorbitan fatty acid esters and polyoxyethylated sorbitan fatty acid esters, and dimethylisosorbitol.

Additionally suitable are interface-active surfactants which have the capacity to exert a positive influence on the stability of the two phase matrix layer, by lowering the interfacial energy.

The water vapor-impermeable polymer is embedded in the matrix. There is therefore virtually no contact between it and the skin, and it therefore does not impair the adherence of the PSA on the skin.

The reduction in water vapor permeability here is based on the lengthening of the effective diffusion pathway for the water molecules. This also means that the extent of the effect is dependent on the amount of dispersed polymer and, of course, on the overall thickness of the matrix layer.

This relationship was investigated experimentally on a polyacrylate adhesive and low molecular mass polyisobutylene. For this purpose, films of adhesive with different thicknesses and different polyisobutylene contents were produced, and the water vapor permeability was measured according to DIN method EN 13726-2 for a sample size of 20 cm$^2$ at 37° C. and 18% relative humidity. The sample composition and the water vapor permeability measured are shown in table 1, and the water vapor permeability additionally in FIG. 3. The water vapor permeability is then situated in general between 50 and 600 g/(m$^2$×24 h), preferably between 100 and 500 g/(m$^2$×24 h), more particularly between 150 and 400 g/(m$^2$×24 h).

TABLE 1

Sample composition and water vapor permeability

| Fraction of polyacrylate adhesive[1] [wt %] | Fraction of polyiso-butylene[2] [wt %] | Basis weight [g/m$^2$] | Water vapor permeability [g/(m$^2$ × 24 h)] |
|---|---|---|---|
| 100 | 0 | 106 | 376 |
| 90 | 10 | 100 | 399 |
| 80 | 20 | 97 | 308 |
| 70 | 30 | 95 | 276 |
| 70 | 30 | 190 | 129 |
| 60 | 40 | 99 | 245 |

[1]DURO-TAK ® 387-2353, Henkel
[2]OPPANOL ® B 10, BASF

As is seen, 10 wt % of polyisobutylene has as yet virtually no effect, 20 wt % already has a marked effect, and at 40 wt % the permeability is almost halved. As expected, the permeability is also dependent on the thickness of the layer; in other words, the permeability is halved by virtue of a doubling.

Furthermore, the influence of the polyisobutylene content on the rate of permeation from a patch system was investigated. The active ingredient selected for this purpose was diclofenac sodium salt, which was incorporated into a single-layer matrix system with a textile backing layer. On the assumption that the hydrophilic active ingredient salt has only negligible solubility in polyisobutylene, the amount of active ingredient was selected such that in all of the samples the active ingredient concentration remained the same in spite of different polyisobutylene contents in the external polyacrylate phase. This ruled out the possibility of differences in the permeation rates arising not only from a difference in the extent of occlusion but also from differences in thermodynamic activities.

The permeation studies were carried out using human epidermis and the Franz diffusion cells, with which the skilled person is very familiar. The values in the tables are the average values from 4 independent experiments in each case.

Figure 4:
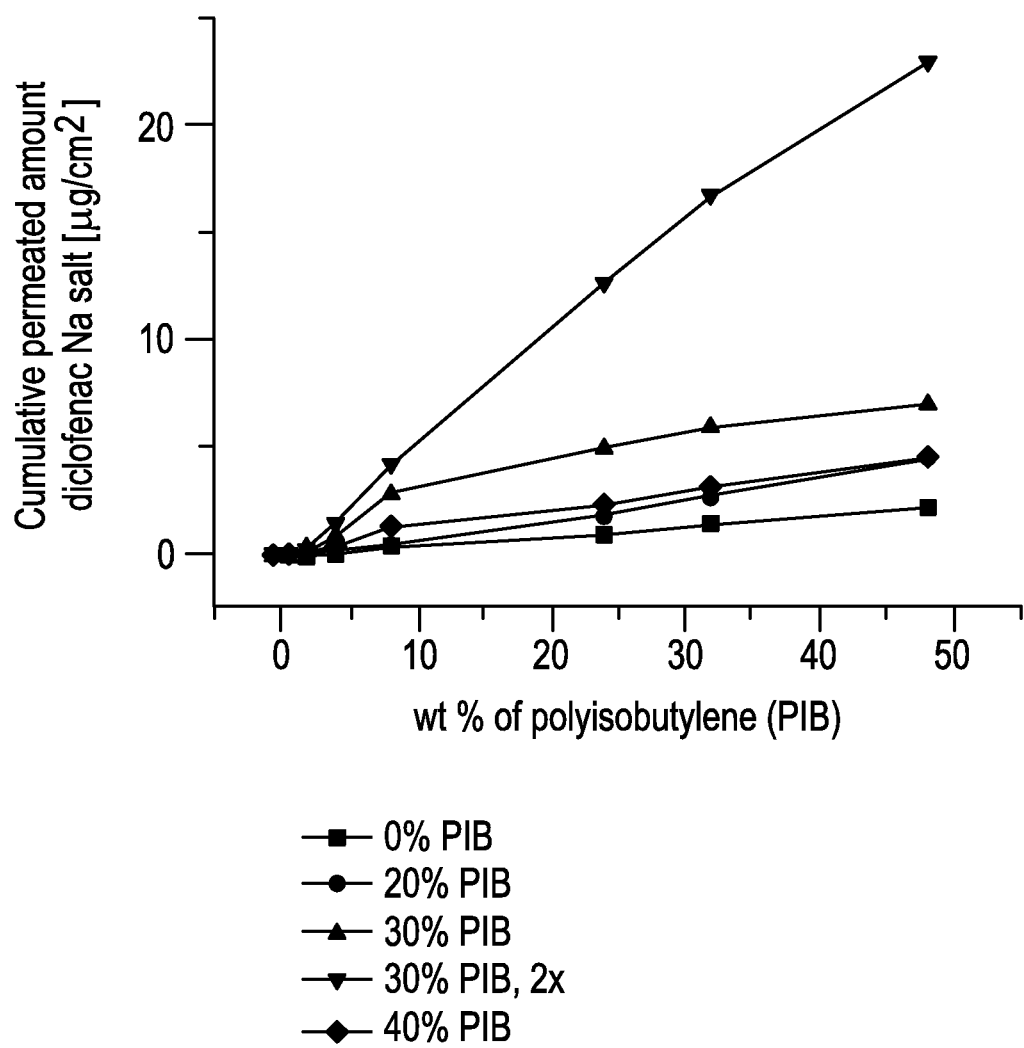
FIG. 4 is a graphical illustration of the fraction of polyisobutylene and cumulatively permeated amount of diclofenac Na salt.

The composition of the samples and the associated permeation rates are summarized in tables 2 and 3, and the permeation rates are additionally shown graphically in FIG. 4.

TABLE 2

Composition of the samples for permeation studies

| Sample number | Parts by wt of DURO-TAK® 387-2353 polyacrylate adhesive | Parts by wt of OPPANOL® B 10 polyiso-butylene | Parts by wt of diclofenac Na salt | Parts by wt of oleic acid | Basic weight [g/m²] |
|---|---|---|---|---|---|
| 1 | 84 | 0 | 6 | 10 | 100 ± 5 |
| 2 | 84 | 20 | 6 | 10 | 100 ± 5 |
| 3 | 84 | 30 | 6 | 10 | 100 ± 5 |
| 4[1)] | 84 | 30 | 6 | 10 | 200 ± 5 |
| 5 | 84 | 40 | 6 | 10 | 100 ± 5 |

[1)] doubled layer thickness relative to sample 3

TABLE 3

Permeation rates using human epidermis

| Sample number | Permeation time and permeated amount of diclofenac Na salt [μg/cm²] | | | | | | |
|---|---|---|---|---|---|---|---|
| | 1 h | 2 h | 4 h | 8 h | 24 h | 32 h | 48 h |
| 1 | 0 | 0.023 | 0.083 | 0.219 | 0.98 | 1.45 | 2.32 |
| 2 | 0 | 0.05 | 0.16 | 0.40 | 1.82 | 2.85 | 4.65 |
| 3 | 0.03 | 0.20 | 0.93 | 2.85 | 5.10 | 5.93 | 7.17 |
| 4[1)] | 0.08 | 0.37 | 1.42 | 4.22 | 12.8 | 16.8 | 23.1 |
| 5 | 0 | 0.10 | 0.37 j | 1.22 | 2.34 | 3.19 | 4.64 |

[1)] doubled layer thickness relative to sample 3

The permeation study results show clearly that the permeation rate is dependent on the amount of polyisobutylene and on the occlusion increased as a result. No other explanation can be contemplated, since the composition of the active ingredient phase is the same across all samples, and the addition of polyisobutylene in fact reduces the relative proportion of said phase in the matrix. However, the optimum for the polyisobutylene content appears to lie at 30 wt %, since 40 wt % exhibits approximately the same result as 20 wt %. With larger amounts, the diminishing proportion of the active ingredient phase, and the lengthening effective diffusion pathway for the active ingredient as well, then have disadvantageous consequences.

Figure 5:
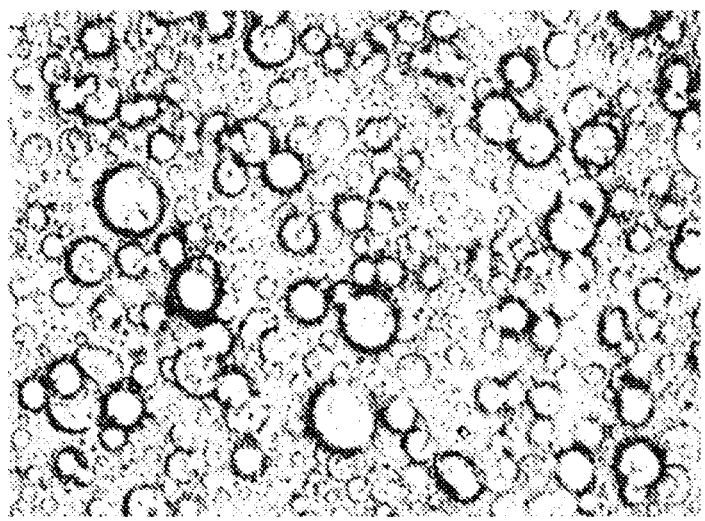
FIG. 5 depicts polyisobutylene particles dispersed in the polyacrylate adhesive phase.

Since the internal phase is separate from the external phase, as shown in FIG. 5, and there is no mixing at a molecular level, the addition of internal phase with low water vapor permeability does not influence the saturation solubility of the active ingredients in the external phase, which consists of polyacrylates or silicones. This means that in systems of this kind, the delivery of active ingredient is unaffected by a change in the saturation solubility in the active ingredient phase, such as in U.S. Pat. No. 6,235,306, for example, stated by way of example. In the formulations identified in table 2 and used in the permeation studies, table 3, the ratio of acrylate adhesive to active ingredient is held the same; accordingly, the differences in the permeation rates measured can be explained only as occlusion increasing in line with the amount of polyisobutylene.

The production examples below serve for illustration of the invention, without the invention being confined thereto.

Example 1

Production of Patches with Diclofenac Sodium Salt as per Formulation 1, 2, 3, 4, and 5

90 g of polyisobutylene (OPPANOL® B 10, BASF) are dissolved in 110 g of n-heptane by stirring. This gives 200 g of polyisobutylene solution with a solids content of 45% w/w.

20 g of diclofenac sodium salt are dissolved with stirring in 774 g of DURO-TAK® 387-2353 (solids content 36%), 150 g of ethyl acetate, and 33 g of oleic acid. This gives 929 g of active ingredient-containing polyacrylate solution with a solids content of 34% w/w.

The coating composition is produced by adding the amounts of polyisobutylene solution indicated in table 4 to 100 g portions of the active ingredient-containing polyacrylate solution.

TABLE 4

Composition of formulations 1 to 5

| Formulation | Polyisobutylne in matrix [% w/w] | Added mass of polyisobutylene solution [g] |
|---|---|---|
| 1 | 0 | 0 |
| 2 | 20 | 15.96 |
| 3, 4 | 30 | 23.91 |
| 5 | 40 | 31.91 |

The dispersions are produced by rapid mechanical stirring at 400 rpm to 10 minutes. The matrices are produced by coating of these dispersions onto a siliconized polyester film 100 μm thick, with subsequent removal of the solvents by drying at 50° C. to 25 minutes. The thickness of the coating film still containing solvent is selected such that the dry matrix film has a basis weight of 110 g/m². The matrix for formulation 4 is obtained by single lamination of the matrix film for formulation 3, already dried, to itself.

The dried films are laminated with a bielastic woven polyester fabric, to give the overall laminate.

The completed patches, and the samples for the permeation studies, are diecut from the overall laminate.

Example 2

Production of a Lidocaine Patch 50 g of lidocaine are dissolved with stirring in
1164 g of polyacrylate solution (DURO-TAK® 387-2052, Henkel, solids content 47% w/w)
74 g of ethanol
110 g of ethyl acetate
6 g of menthol
100 g of oleic acid.

Dispersed in this solution are 631 g of a polyisobutylene solution (48% w/w in n-heptane). The composition is coated onto a siliconized polyester film, in a thickness such that removal of the solvents (10 minutes at room temperature, 25 minutes at 50° C.) results in basis weight of 135 g/m². The dried film is laminated with a bielastic woven polyester fabric, to give the overall laminate.

BRIEF DESCRIPTION OF THE DRAWINGS AND THE REFERENCE SYMBOLS

Figure 1:
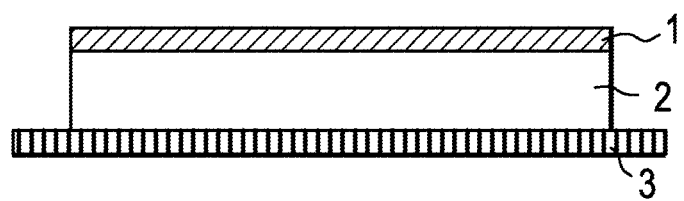
FIG. 1 is a schematic illustration of an occlusive patch with a water vapor-impermeable backing layer.
Figure 3:
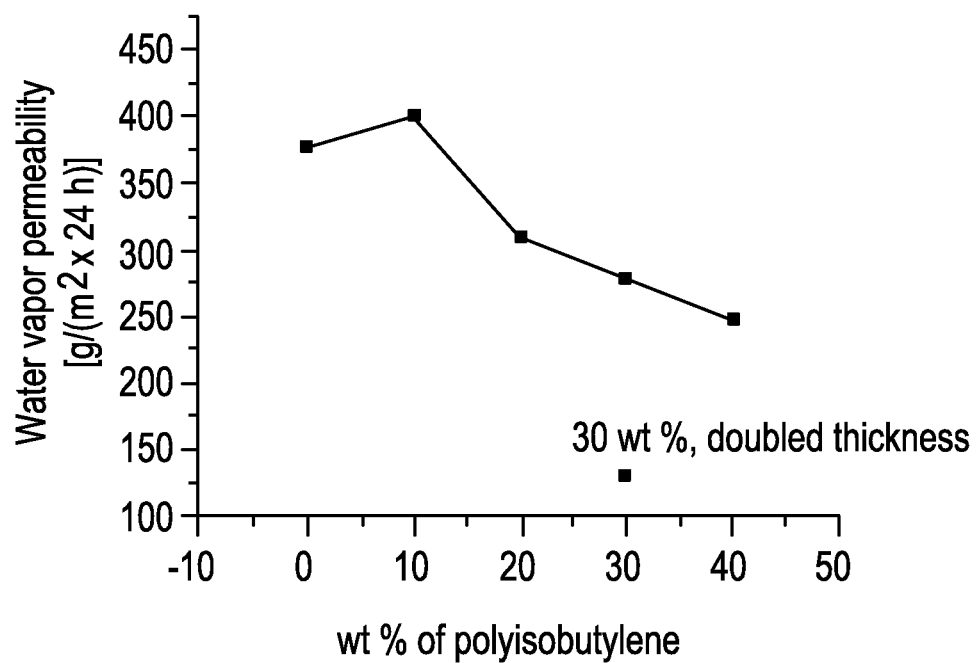
FIG. 3 is a graphical illustration of water vapor permeability as a function of polyisobutylene content and matrix layer thickness.

FIG. 1: occlusive patch with water vapor-impermeable backing layer
  1 water vapor-impermeable backing layer
  2 active ingredient matrix
  3 redetachable protective film
FIG. 2: inventive patch with adjustable occlusion
  4 backing layer of textile material
  5 structure-forming base polymer
  6 particles of the polymer with relatively low water vapor permeability
  7 redetachable protective film FIG. 3: water vapor permeability as a function of polyisobutylene content and matrix layer thickness FIG. 4: fraction of polyisobutylene and cumulatively permeated amount of diclofenac Na salt FIG. 5: polyisobutylene particles dispersed in the polyacrylate adhesive phase (scale: 500:1)

The invention claimed is:

1. A transdermal or topical active ingredient patch having a nonocclusive backing layer which consists of a textile material, a matrix formed from one or more polymer layers, with at least one active pharmaceutical ingredient in one or more of the layers, wherein the structure-forming base polymers of the layer or layers of the matrix layer which makes contact with the skin on application are nonocclusive or minimally occlusive and are pressure-sensitive adhesives and in at least one of the polymer layers there is a second polymer dispersed, which is immiscible or very minimally miscible with the base polymer and has a low water vapor permeability, which is polyisobutylene, a styrene-isoprene-styrene block polymer or a styrene-butadiene-styrene block polymer, the fraction of dispersed particles of the second polymer being between 7 and 40%, whereby said patch has a water vapor permeability of between 50 and 600 g/(m2×24 h).

2. The transdermal or topical patch of claim 1, wherein the pressure-sensitive adhesive is a polyacrylate adhesive.

3. The transdermal or topical patch of claim 1, wherein the pressure-sensitive adhesive is a silicone adhesive.

4. The transdermal or topical patch of claim 1, wherein the pressure-sensitive adhesive is a polyacrylate adhesive or a silicone adhesive and the matrix is single-layer.

5. The transdermal or topical patch of claim 1, wherein the polymer with low water vapor permeability, dispersed in the base polymer forms a phase having an average particle size of 5 to 50 μm.

6. The transdermal or topical patch of claim 5, wherein the fraction of the dispersed particles of the polymer with low water vapor permeability is between 10 and 30 wt %.

7. The transdermal or topical patch of claim 1, wherein the basis weight of the matrix is between 50 and 400 g/m2.

8. The transdermal or topical patch claim 1, wherein said patch has a water vapor permeability as measured by the DIN method EN 13726-2 for a sample size of 20 cm2 at 37° C. and 18% relative humidity of between 50 and 600 g/(m2×24 h).

9. The transdermal or topical patch of claim 1, wherein the active pharmaceutical ingredient is a nonsteroidal anti-inflammatory drug.

10. The transdermal or topical patch of claim 9, wherein the active pharmaceutical ingredient is diclofenac or a pharmaceutically acceptable salt thereof, ketoprofen, ibuprofen, flurbiprofen, naproxen, tiaprofenic acid, indomethacin, piroxicam, tenoxicam, meloxicam, flufenaminic acid, or mefenaminic acid.

11. The transdermal or topical patch of claim 10, wherein the active pharmaceutical ingredient is a diclofenac salt.

12. The transdermal or topical patch of claim 1, wherein the active pharmaceutical ingredient is a topically active analgesic.

13. The transdermal or topical patch of claim 12, wherein the topically active analgesic is lidocaine or tetracaine.

14. The transdermal or topical patch of claim 1, wherein the matrix comprises at least one permeation enhancer.

15. The transdermal or topical patch of claim 14, wherein the permeation enhancer or enhancers are low molecular mass, monohydric or polyhydric alcohols, fatty acids, fatty alcohols, fatty alcohol ethers, polyoxyethylated fatty alcohols, fatty acid esters, sorbitan fatty acid esters, polyoxyethylated sorbitan fatty acid esters, and/or dimethylisosorbitol.

16. The transdermal or topical patch of claim 5, wherein the polymer with low water vapor permeability has an average particle size of 7 to 40 μm.

17. The transdermal or topical patch of claim 5, wherein the polymer with low water vapor permeability has an average particle size of 10 to 30 μm.

18. The transdermal or topical patch of claim 7, wherein the basis weight of the matrix is between 60 and 300 g/m2.

19. The transdermal or topical patch of claim 7, wherein the basis weight of the matrix is between 70 and 200 g/m2.

20. The transdermal or topical patch of claim 8, wherein said patch has a water vapor permeability of between 100 and 500 g/(m2×24 h).

21. The transdermal or topical patch of claim 8, wherein said patch has a water vapor permeability of between 150 and 400 g/(m2×24 h).

22. The transdermal or topical patch of claim 11, wherein the diclofenac salt is a diclofenac sodium salt, diclofenac potassium salt, diclofenac diethylammonium salt, or the dihydroxyethylpyrrolidine salt of diclofenac.

23. The transdermal or topical patch of claim 14, wherein the matrix comprises at least one permeation enhancer in the structure-forming base polymer.

24. The transdermal or topical patch of claim 15, wherein the fatty acid is oleic acid.

\* \* \* \* \*

UNITED STATES PATENT AND TRADEMARK OFFICE
CERTIFICATE OF CORRECTION

| | | |
|---|---|---|
| PATENT NO. | : 9,180,103 B2 | Page 1 of 1 |
| APPLICATION NO. | : 14/346527 | |
| DATED | : November 10, 2015 | |
| INVENTOR(S) | : Walter Müller et al. | |

It is certified that error appears in the above-identified patent and that said Letters Patent is hereby corrected as shown below:

In The Claims

Claim 1, line 23, delete "40%" insert --40 wt. %--

Signed and Sealed this
Twenty-third Day of February, 2016

Michelle K. Lee
*Director of the United States Patent and Trademark Office*